United States Patent
Ku

(10) Patent No.: US 10,124,674 B2
(45) Date of Patent: Nov. 13, 2018

(54) VEHICLE SAFETY DETECTING RING AND VEHICLE STEERING WHEEL

(71) Applicant: ScienBiziP Consulting (Shenzhen) Co., Ltd., Shenzhen (CN)

(72) Inventor: Ping-Han Ku, New Taipei (TW)

(73) Assignee: ScienBiziP Consulting (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 15/688,873

(22) Filed: Aug. 29, 2017

(65) Prior Publication Data
US 2018/0162224 A1 Jun. 14, 2018

(30) Foreign Application Priority Data
Dec. 14, 2016 (TW) .............................. 105141372 A

(51) Int. Cl.
| G08B 23/00 | (2006.01) |
| B60K 28/06 | (2006.01) |
| A61B 5/18 | (2006.01) |
| G08B 21/06 | (2006.01) |
| B62D 15/00 | (2006.01) |

(52) U.S. Cl.
CPC .............. *B60K 28/066* (2013.01); *A61B 5/18* (2013.01); *G08B 21/06* (2013.01); *B62D 15/00* (2013.01)

(58) Field of Classification Search
CPC ........ B60K 28/066; A61B 5/18; G08B 21/06; B62D 15/00
USPC ......................................................... 340/576
See application file for complete search history.

(56) References Cited

U.S. PATENT DOCUMENTS

| 5,874,892 | A  | * | 2/1999  | Antonellis | B60Q 1/52 180/271 |
| 6,609,768 | B1 | * | 8/2003  | Frank      | B60T 7/107 200/61.57 |
| 7,468,656 | B1 | * | 12/2008 | Frank      | B60Q 1/0082 340/468 |
| 7,710,279 | B1 | * | 5/2010  | Fields     | G08B 21/06 340/309.16 |
| 8,095,270 | B2 | * | 1/2012  | Bossler    | B62D 1/06 280/735 |
| 8,451,109 | B1 | * | 5/2013  | Daniel     | B62D 1/046 340/438 |
| 8,731,645 | B2 | * | 5/2014  | Kato       | A61B 5/0408 600/509 |
| 9,159,221 | B1 | * | 10/2015 | Stantchev  | G08C 17/02 |
| 2003/0189493 | A1 | * | 10/2003 | Klausner | B62D 1/046 340/575 |
| 2004/0209594 | A1 | * | 10/2004 | Naboulsi | B60R 11/0264 455/404.1 |
| 2004/0243013 | A1 | * | 12/2004 | Kawachi  | A61B 5/18 600/509 |

(Continued)

*Primary Examiner* — Zhen Y Wu
(74) *Attorney, Agent, or Firm* — ScienBiziP, P.C.

(57) ABSTRACT

A vehicle safety detecting ring includes a ring body, at lease one detector, a touching area and an alarm device. The ring body is configured to mounted on a steering wheel. The at least one detector is located inside the ring body and configured to detect information of driver. The touching area is connected with the at least one detector in the ring body to transmit the information of driver to the at least one detector. The alarm connects with the at least one detector and is configured to issue an alarm when the at least one detector detects an abnormal signal.

20 Claims, 3 Drawing Sheets

(56) References Cited

U.S. PATENT DOCUMENTS

| | | | |
|---|---|---|---|
| 2009/0076637 A1* | 3/2009 | Kameyama | G06F 17/30764 |
| | | | 700/94 |
| 2010/0028210 A1* | 2/2010 | Ozaki | B60K 28/063 |
| | | | 422/84 |
| 2010/0039224 A1* | 2/2010 | Okude | B60R 25/25 |
| | | | 340/5.83 |
| 2011/0304446 A1* | 12/2011 | Basson | B60K 28/063 |
| | | | 340/438 |
| 2012/0256769 A1* | 10/2012 | Satpathy | G08B 13/19647 |
| | | | 340/989 |
| 2013/0141342 A1* | 6/2013 | Bokma | G06F 3/03547 |
| | | | 345/173 |
| 2014/0292692 A1* | 10/2014 | Okuyama | B62D 1/046 |
| | | | 345/173 |
| 2017/0161576 A1* | 6/2017 | Banno | G06K 9/00845 |
| 2017/0166236 A1* | 6/2017 | Iguchi | B62D 1/046 |
| 2017/0341676 A1* | 11/2017 | Clochard | B62D 1/046 |

\* cited by examiner

VEHICLE SAFETY DETECTING RING AND VEHICLE STEERING WHEEL

CROSS-REFERENCE TO RELATED APPLICATIONS

This application claims all benefits accruing under 35 U.S.C. § 119 from Taiwan Patent Application No. 105141372, filed on Dec. 14, 2016, in the Taiwan Intellectual Property Office, the contents of which are hereby incorporated by reference.

FIELD

The subject matter herein generally relates to a vehicle safety detecting ring and a vehicle steering wheel using the same.

BACKGROUND

With the continuous increase of vehicle, vehicle driving safety has bring more and more attention. Conventionally, in order to improve driving safety performance of vehicle, hardware design of vehicle is often improved, such as strengthening the body, improve the airbag and so on. But, these measures can not be used to avoid vehicle accidents to increase vehicle driving safety.

Further, the steering wheel of traditional vehicle can only be used to simply control direction, and there is no detection to confirm the driver's driving condition, and it is easy to cause an accident due to driver's fatigue driving or physical illness.

What is needed, therefore, is to provide a vehicle safety detecting ring and a car steering wheel using the same which can overcome the shortcomings as described above.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

Figure 1:
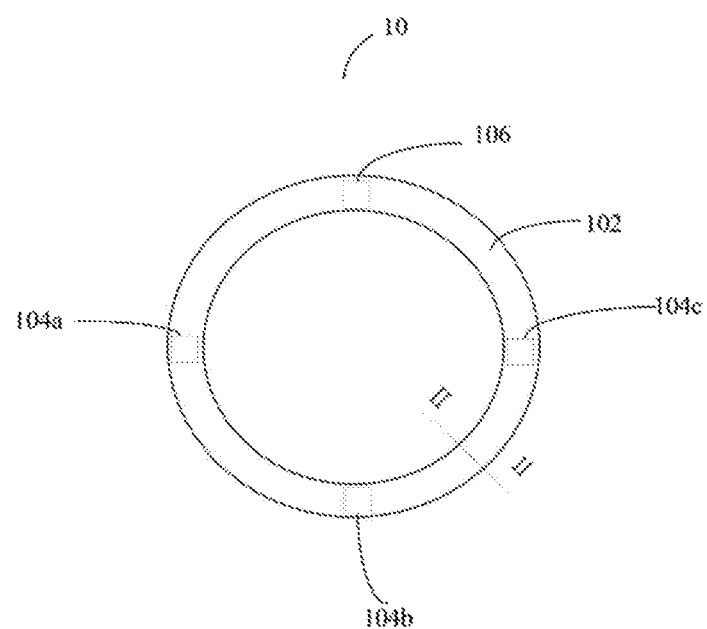
FIG. 1 is a schematic top view of a vehicle safety detecting ring provided according to embodiment of the present invention.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The connection can be such that the objects are permanently connected or releasable connected. The term "substantially" is defined to be essentially conforming to the particular dimension, shape or other word that substantially modifies, such that the component need not be exact. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

The present disclosure relates to a vehicle safety detecting ring and a vehicle steering wheel described in detail as below.

Referring to FIG. 1, a vehicle safety detecting ring 10 is provided according to one embodiment. The vehicle safety detecting ring 10 includes a ring body 100, at least one detector 104, a touch area 102 and an alarm device 106. The ring body 100 has a hollow structure and can be mounted on a steering wheel. The at least one detector 104 is located inside the ring body 100, and is used to detect driver's information. The touch area 102 is located on a surface of the hollow ring body 100. The touch area 102 is connected with the at least one detector 104 inside of the hollow ring body 100 to transmit the driver's information to the at least one detector 104. The alarm device 106 is connected with the at least one detector 104. The alarm device 106 is used to issue an alarm when the at least one detector 104 detect an abnormal signal.

Figure 2:
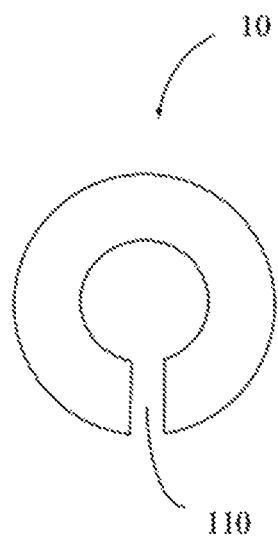
FIG. 2 is a cross-sectional view taken along the line II-II in FIG. 1.

A material of the ring body 100 can be a flexible material. Referring to FIG. 2, the ring body 100 is a hollow structure with an opening 110. A cross sectional shape of the ring body 100 is a C-type structure. The ring body 100 can be fitted on a steering wheel through the opening 110.

The at least one detector 104 is used to detect information of the driver. The driver's information includes the driver's blood pressure, the pulse, the fingerprint, the holding strength on the steering wheel, and the like. The at least one detector 104 is built into the ring body 100. The at least one detector 104 can be one detector 104 or a plurality of detectors 104. In the embodiment according to FIG. 2, there are three detectors 104 located in the ring body 100. The three detectors 104 include a first detector 104a, a second detector 104b and a third detector 104c. The first detector 104a, the second detector 104b and the third detector 104c are sequentially distributed inside the ring body 100. The first detector 104a is used to store and recognize a fingerprint information of the driver. The second detector 104b is used to store and measure a blood pressure pulse information of the driver. The third detector 104c is used to detect a surface pressure applied on the ring body 100 by the driver to determine whether the driver's hands leave the steering wheel. In other embodiment, the vehicle safety detecting ring 10 can further include more detectors 104 to detect additional information of the driver. In other embodiments, the detector 104 may also be a detector having a plurality of functions, and can have functions of measuring blood pressure, pulse, fingerprint, pressure, and the like.

The touch area 102 is connected to the at least one detector 104 and transmits a signal to the detector 104 by touching of the driver's hand. The touch area 102 may be a whole surface of the entire ring body 100. The driver's information can be transmitted to the at least one detector 104 through the touch area 102 regardless of where the driver's hand is placed in the vehicle safety detecting ring 10. In other embodiments, the touch area 102 may also be divided into a plurality of modules distributed in areas where the driver frequently touches.

The alarm device 106 is located in the ring body 100. The alarm device 106 is connected to the at least one detector 104 and the alarm device 106 issues an alarm when the driver's information detected by the detector 104 exceeds the standard range or does not correspond to the stored information. In the present embodiment, when the fingerprint of the driver detected by the first detector 104*a* is not stored in the vehicle safety detecting ring 10, the drive is judged as a stranger, and the alarm device 106 can issue an alarm to prevent the vehicle from being stolen; when the second detector 104*b* detects that the driver's blood pressure or the pulse exceeds the standard range, the alarm device 106 issues an alarm to alert the driver for physical condition and safe driving; when the third detector 104*c* does not sense the pressure by the driver inside the touch area 102, it is judged that the driver's hands leave the steering wheel and when the time of leaving the steering wheel exceeds a predetermined time, the alarm device 106 issues an alarm to alert the driver for safe driving or to cause the vehicle to brake urgently.

The vehicle safety detecting ring provided by the invention can detect the driver's information through the touch area to monitor the driver's safe driving, avoid the occurrence of an accident and improve the safety performance of the vehicle. At the same time, the vehicle safety detecting ring can judge the driver's fingerprint to prevent the vehicle from been stolen.

Figure 3:
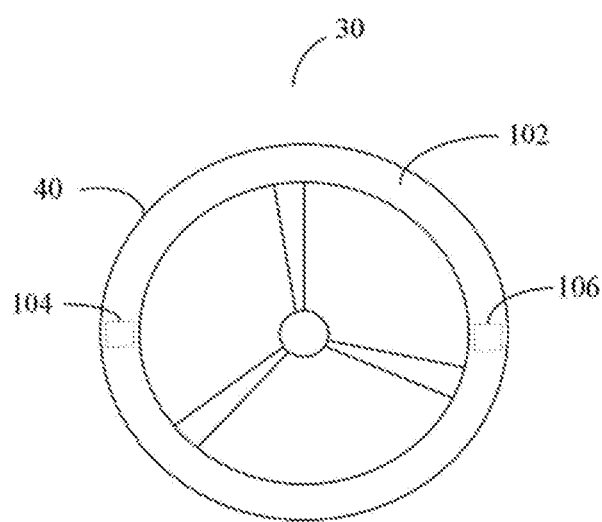
FIG. 3 is a schematic structural view of an vehicle steering wheel according to one embodiment of the present invention.

Referring to FIG. 3, a vehicle steering wheel 30 according to one embodiment is provided. The vehicle steering wheel 30 includes a steering wheel frame 40, at least one detector 204, a touch area 202 and an alarm device 206. The steering wheel frame 40 includes a cross structure and a ring structure. The at least one detector 204 built in the steering wheel frame 40 and is used to detect information of the driver. The touch area 202 is located on a surface of the ring structure. The touch area 202 is connected to at least one detector 204 inside of the steering wheel frame 40 to transmit the driver information to the at least one detector 204. The alarm device 206 is connected to the at least one detector 204.

Characteristics of the at least one detector 204 are the same as the at least one detector 104 in the vehicle safety detection ring 10 disclosed above.

Characteristics of the touch area 202 are the same as the touch area 102 in the vehicle safety detection ring 10 disclosed above.

Characteristics of the alarm device 206 are the same as the alarm device 106 in the vehicle safety detection ring 10 disclosed above.

The vehicle steering wheel provided by the invention can detect the driver's information through the touch area to monitor the driver's safe driving, avoid the occurrence of the accident and further improve the safety performance of the vehicle. At the same time, the steering wheel can be used to determine the driver's fingerprint to prevent the vehicle from been stolen.

The embodiments shown and described above are only examples. Even though numerous characteristics and advantages of the present technology have been set forth in the forego description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

Depending on the embodiment, certain of the steps of methods described may be removed, others may be added, and the sequence of steps may be altered. The description and the claims drawn to a method may include some indication in reference to certain steps. However, the indication used is only to be viewed for identification purposes and not as a suggestion as to an order for the steps.

What is claimed is:

1. A vehicle safety detecting ring comprising:
 a ring body configured to be mounted on a steering wheel, wherein a material of the ring body is a flexible material, the ring body is a hollow structure with an open, and cross sectional shape of the ring body is a C-type structure, so that the ring body is fitted on the steering wheel through the opening;
 at least one detector located inside the ring body and being configured to detect information of a driver, the at least one detector detects a surface pressure applied on the ring body by the driver to determine whether the driver's hands leave the steering wheel exceeds a predetermined time and causes the vehicle to brake urgently;
 a touching area defined on an outside surface of the ring body and connected with the at least one detector in the ring body to transmit the information of the driver to the at least one detector; and
 an alarm inside the ring body, connected with the at least one detector and being configured to issue an alarm when the at least one detector detects an abnormal signal according to the detected information.

2. The vehicle safety detecting ring of claim 1, wherein the information of the driver comprises a blood pressure, a pulse, a fingerprint and a holding strength on the steering wheel.

3. The vehicle safety detecting ring of claim 1, wherein the at least one detector comprises one detector or a plurality of detectors.

4. The vehicle safety detecting ring of claim 1, wherein the at least one detector comprises a first detector, a second detector and a third detector sequentially distributed inside the ring body.

5. The vehicle safety detecting ring of claim 4, wherein the first detector is configured to store and recognize a fingerprint information of the driver; when the fingerprint of the driver detected by the first detector is not stored in the vehicle safety detecting ring, the driver is judged as a stranger, and the alarm device issues an alarm to prevent the vehicle from being stolen.

6. The vehicle safety detecting ring of claim 4, wherein the second detector is configured to store and measure a blood pressure or a pulse information of the driver; when the second detector detects that the driver's blood pressure or the pulse exceeds a standard range, the alarm device issues an alarm to alert the driver for physical condition and safe driving.

7. The vehicle safety detecting ring of claim 4, wherein the third detector is used to detect the surface pressure applied on the ring body by the driver to determine whether the driver's hands leave the steering wheel; when the third detector detects that the driver's hands leave the steering wheel and when a time of leaving the steering wheel exceeds the predetermined time, the alarm device issues an alarm to alert the driver for safe driving or to cause the vehicle to brake urgently.

8. The vehicle safety detecting ring of claim 1, wherein the touching area is connected to the at least one detector and transmits a signal to the detector by touching of the driver's hand.

9. The vehicle safety detecting ring of claim 1, wherein the touching area is a whole surface of the entire ring body.

10. The vehicle safety detecting ring of claim 1, wherein the touching area comprises a plurality of parts distributed in areas where the driver frequently touches.

11. The vehicle safety detecting ring of claim 1, wherein the alarm device is connected to the at least one detector and the alarm device issues an alarm when the driver's information detected by the detector exceeds a standard range.

12. A vehicle steering wheel comprising:
a steering wheel frame;
a ring body mounted on the steering wheel frame, wherein a material of the ring body is a flexible material, the ring body is a hollow structure with an open, and cross sectional shape of the ring body is a C-type structure, so that the ring body is fitted on the steering wheel frame through the opening
at least one detector located inside the ring body and being configured to detect information of a driver, the at least one detector detects a surface pressure applied on the ring body by the driver to determine whether the driver's hands leave the steering wheel exceeds a predetermined time and causes the vehicle to brake urgently;
a touching area defined on an outside surface of the ring body and connected with the at least one detector in the ring body to transmit the information of the driver to the at least one detector; and
an alarm inside the ring body, connecting with the at least one detector and being configured to issue an alarm when the at least one detector detects an abnormal signal.

13. The vehicle steering wheel of claim 12, wherein the at least one detector comprises a first detector configured to detect and recognize a fingerprint information of the driver; when the fingerprint of the driver detected by the first detector is not stored in the vehicle safety detecting ring, the driver is judged as a stranger, and the alarm device issues an alarm to prevent the vehicle from being stolen.

14. The vehicle steering wheel of claim 12, wherein the at least one detector comprises a second detector configured to detect and monitor a blood pressure or a pulse of the driver; when the second detector detects that the driver's blood pressure or the pulse exceeds a standard range, the alarm device issues an alarm to alert the driver for physical condition and safe driving.

15. The vehicle steering wheel of claim 12, wherein the at least one detector comprises a third detector configured to detect the surface pressure applied on the ring body by the driver to determine whether the driver's hands leave the steering wheel; when the third detector detects that the driver's hands leave the steering wheel and when the time of leaving the steering wheel exceeds a predetermined time, the alarm device issues an alarm to alert the driver for safe driving.

16. The vehicle steering wheel of claim 12, wherein the at least one detector comprises a third detector configured to detect a surface pressure applied on the ring body by the driver to determine whether the driver's hands leave the steering wheel; when the third detector detects that the driver's hands leave the steering wheel and when a time of leaving the steering wheel exceeds a predetermined time, the alarm device issues an alarm to cause the vehicle to brake urgently.

17. A vehicle steering wheel comprising:
a steering wheel frame; and
a vehicle safety detecting ring detachably mounted on the steering wheel frame, wherein the vehicle safety detecting ring comprises:
a flexible ring body configured to be detachably mounted on the steering wheel frame, wherein the flexible ring body is a hollow structure with an open, and cross sectional shape of the flexible ring body is a C-type structure, so that the flexible ring body is fitted on the steering wheel frame through the opening;
at least one detector located inside the ring body and being configured to detect information of a driver, the at least one detector detects a surface pressure applied on the ring body by the driver to determine whether the driver's hands leave the steering wheel exceeds a predetermined time and causes the vehicle to brake urgently;
a touching area defined on an outside surface of the ring body and connected with the at least one detector in the ring body to transmit the information of the driver to the at least one detector; and
an alarm inside the ring body, connecting with the at least one detector and being configured to issue an alarm when the at least one detector detects an abnormal signal.

18. The vehicle steering wheel of claim 17, wherein the at least one detector comprises a first detector configured to detect and recognize a fingerprint information of the driver; when the fingerprint of the driver detected by the first detector is not stored in the vehicle safety detecting ring, the driver is judged as a stranger, and the alarm device issues an alarm to prevent the vehicle from being stolen.

19. The vehicle steering wheel of claim 17, wherein the at least one detector comprises a second detector configured to detect and monitor a blood pressure or a pulse of the driver; when the second detector detects that the driver's blood pressure or the pulse exceeds a standard range, the alarm device issues an alarm to alert the driver for physical condition and safe driving.

20. The vehicle steering wheel of claim 17, wherein the at least one detector comprises a third detector configured to detect the surface pressure applied on the ring body by the driver to determine whether the driver's hands leave the steering wheel; when the third detector detects that the driver's hands leave the steering wheel and when the time of leaving the steering wheel exceeds a predetermined time, the alarm device issues an alarm to alert the driver for safe driving or to cause the vehicle to brake urgently.

* * * * *